(12) United States Patent
Shan

(10) Patent No.: US 8,728,972 B2
(45) Date of Patent: *May 20, 2014

(54) HIGH PORE VOLUME VPO CATALYST FOR MALEIC ANHYDRIDE PRODUCTION

(75) Inventor: Zhiping Shan, The Woodlands, TX (US)

(73) Assignee: Huntsman Petrochemical LLC, The Woodlands, TX (US)

( * ) Notice: Subject to any disclaimer, the term of this patent is extended or adjusted under 35 U.S.C. 154(b) by 200 days.

This patent is subject to a terminal disclaimer.

(21) Appl. No.: 13/123,872

(22) PCT Filed: Oct. 8, 2009

(86) PCT No.: PCT/US2009/059932
§ 371 (c)(1),
(2), (4) Date: Apr. 12, 2011

(87) PCT Pub. No.: WO2010/047957
PCT Pub. Date: Apr. 29, 2010

(65) Prior Publication Data
US 2011/0201830 A1    Aug. 18, 2011

Related U.S. Application Data

(60) Provisional application No. 61/107,228, filed on Oct. 21, 2008, provisional application No. 61/147,564, filed on Jan. 27, 2009.

(51) Int. Cl.
*B01J 20/34* (2006.01)
*B01J 38/50* (2006.01)
*B01J 38/52* (2006.01)
*B01J 27/198* (2006.01)

(52) U.S. Cl.
USPC .......................................................... 502/209

(58) Field of Classification Search
USPC .......................................................... 502/209
See application file for complete search history.

(56) References Cited

U.S. PATENT DOCUMENTS

| 4,092,269 | A |   | 5/1978  | Mount et al. |
| 4,359,405 | A |   | 11/1982 | Mount et al. |
| 4,392,986 | A | * | 7/1983  | Yang et al. ................... 502/209 |
| 4,668,652 | A | * | 5/1987  | Fumagalli et al. ............ 502/209 |
| 4,699,985 | A |   | 10/1987 | Bither, Jr. |
| 4,824,819 | A | * | 4/1989  | Edwards et al. .............. 502/209 |
| 5,137,860 | A |   | 8/1992  | Ebner et al. |
| 5,168,090 | A |   | 12/1992 | Ebner et al. |
| 5,275,996 | A |   | 1/1994  | Andrews et al. |

(Continued)

FOREIGN PATENT DOCUMENTS

WO    2008/030714 A    3/2008

OTHER PUBLICATIONS

Zazhigalov, et al. "Effect of the Pore Structure and Granule Shape of V-P-O Catalyst on the Selectivity of Oxidation of n-Butane" Zhurnal Prikladnoi Kimii, vol. 61, No. 1, p. 101-105 (Jan. 1988). Dielectric Constant Reference Guide Datasheet (Online) Clipper Controls Inc. 2003.

*Primary Examiner* — Patricia L Hailey
(74) *Attorney, Agent, or Firm* — Huntsman International LLC

(57) ABSTRACT

Embodiments of the present invention disclose improved micro-pore catalyst structures containing catalytic material comprised of mixed oxides of vanadium and phosphorus and using such improved micro-pore catalyst structures for the production of maleic anhydride.

12 Claims, 14 Drawing Sheets

(56) References Cited

U.S. PATENT DOCUMENTS

| | | |
|---|---|---|
| 5,773,382 A | 6/1998 | Mitchell et al. |
| 6,495,486 B1 * | 12/2002 | Kamiya et al. ............... 502/172 |
| 7,060,649 B2 * | 6/2006 | Weiguny et al. ............. 502/209 |
| 8,143,461 B2 * | 3/2012 | Forkner ....................... 568/956 |
| 8,404,614 B2 * | 3/2013 | Shan ............................. 502/208 |
| 2004/0014990 A1 | 1/2004 | Storck et al. |
| 2007/0032377 A1 | 2/2007 | Hibst et al. |

* cited by examiner

US 8,728,972 B2

HIGH PORE VOLUME VPO CATALYST FOR MALEIC ANHYDRIDE PRODUCTION

CROSS-REFERENCE TO RELATED APPLICATIONS

This application is the National Phase of International Application PCT/US2009/059932 filed Oct. 8, 2009 which designated the U.S. and which claims priority to U.S. Provisional App. Ser. No. 61/107,228 filed Oct. 21, 2008 and U.S. Provisional App. Ser. No. 61/147,564 filed Jan. 27, 2009. The noted applications are incorporated herein by reference.

STATEMENT REGARDING FEDERALLY SPONSORED RESEARCH OR DEVELOPMENT

Not applicable.

FIELD OF THE INVENTION

This invention relates to catalysts essentially containing vanadium, phosphorus and oxygen ("VPO catalysts") useful in a process for the oxidation of hydrocarbons to dicarboxylic acid anhydrides, for instance, maleic anhydride, and more particularly to a high micro-pore catalyst which provides improved catalytic performance.

BACKGROUND OF THE INVENTION

Numerous VPO catalysts (sometimes referred to as mixed oxides of vanadium and phosphorus), substantially in the form of vanadyl pyrophosphate, optionally containing a promoter component, have been previously disclosed as being useful for the conversion of various hydrocarbon feed stocks to maleic anhydride. In general, such catalysts wherein the valence of the vanadium is less than +5, usually between about +3.8 and about +4.5, are considered particularly well suited for the production of maleic anhydride from hydrocarbons having at least four carbon atoms in a straight chain or cyclic structure. Common organic feed stocks include various hydrocarbons such as n-butane, 1- and 2-butenes, 1,3-butadiene, benzene or mixtures thereof.

VPO catalysts are usually prepared by contacting vanadium-containing compounds, phosphorus-containing compounds, and promoter component-containing compounds (when a promoter element is desired) under certain conditions sufficient to reduce pentavalent vanadium to the tetravalent state and form the desired catalyst precursor comprising vanadyl hydrogen phosphate, optionally containing a promoter component. The catalyst precursor is recovered by separation such as filtration and typically in particulate form having particle size ranging from few microns to hundred microns. Then the precursor is formed into a certain shaped body such as tablet or pellet by compression. Typically, a lubricant such as graphite or boron nitrate is blended into the precursor composition before compression to facilitate the tableting or pelletizing process. Finally the shaped body undergoes a step called activation, which is carried out under certain atmosphere and temperature program, to transfer the catalyst precursor into an active catalytic component.

In its final form, the catalyst comprises a mass of porous tablets or pellets which are charged in bulk to provide the catalyst bed of a fixed bed reactor. Typically, the catalyst is charged to a tubular reactor comprising the tubes of a shell and tube heat exchanger. Hydrocarbon(s) and oxygen are fed to the tubes, and a heat transfer fluid, such as molten salt, is circulated through the shell to remove the exothermic heat of the oxidation reaction.

The porous nature of the catalyst contributes substantially to the active surface area at which the catalytic reaction takes place. For the internal surfaces of the catalyst body (tablets or pellets) to be utilized effectively, the feed gases, hydrocarbon and oxygen, must diffuse through the pores to reach the internal surfaces, and the reaction products must diffuse away from those surfaces and out of the catalyst body.

It is known in the art that resistance to internal diffusion in the catalyst bodies can become a rate limiting factor in the reaction. One method used to overcome resistance to internal is to shorten the diffusion paths by using relatively small catalyst granules. However, small catalyst granules will results in increased pressure drop through the fixed bed, leading to operational difficulties.

Another method used to increase catalytic performance has been to focus on increasing and modifying the catalyst's macro-pore structure. As mentioned above, during the preparation of VPO catalyst, catalyst precursor is compressed into various shapes of tablets or pellets. Inside of the tablets or pellets, pores are formed. There are some micro-pores having pore diameter ranging from 0.01 to, and including, 0.6 microns. These micro-pores are inherently formed among catalyst precursor particles by packing these precursor particles together. Macro-pores, however, are pores with a pore diameter ranging from above 0.6 to about 10 microns that are not inherently formed, rather are formed using pore building agents. Mount et al. in U.S. Pat. No. 4,092,269 disclose that a desired fraction of macro-pores having a size of 0.8 to 10 microns are prepared by adding a pore modification agent to the precursor at any stage prior to activation. After precursor with pore modification agent was compressed into a certain shape, the pore modification agent is removed to generate the macro-pores. Typically, to remove the pore modification agent, calcination of the precursor is common method conducted at a temperature between about 300° C. and 600° C. U.S. Pat. Nos. 4,699,985; 5,773,382 and 5,275,996 also describe the preparation of a maleic anhydride catalyst using pore building agent to generate macro-pore structure.

Increasing pore volume by adding macro-pores is reported to increase catalytic activity. For example, Zazhigalov, et al, "Effect of the Pore Structure and Granule Shape of V-P-O Catalyst on the Selectivity of Oxidation of n-Butane," Zhurnal Prikladnoi Kimii, Vol. 61, No. 1, pp. 101-105 (January, 1988) report that the activity of VPO catalysts in the oxidation of n-butane increases with an increase in the total pore volume and the introduction of macro-pore having pore diameter bigger than 0.8 microns. However, greater efficiency continues to be desired for these catalysts.

SUMMARY OF THE INVENTION

To address the above needs, embodiments of the present invention disclose active VPO catalysts having porous structures such that internal diffusion resistance may be minimized and productivity may be enhanced. It is believed that further increase of micro-pore volume and improvement of pore structure will lead to improved catalyst performance in anhydride production. By the term "improved catalytic performance" it is meant there is an improvement in at least one of the catalyst properties, which properties include yield, selectivity, conversion; yield, selectivity or conversion performance over time, and operability.

Embodiments of the present invention disclose a catalyst for the catalytic oxidation of hydrocarbons to produce a carboxylic acid anhydride comprising an active VPO catalyst, wherein the active VPO catalyst is characterized by: (i) having a total pore volume, micro-pores and a micro-pore volume, wherein the micro-pores are pores on the active VPO catalyst that each have a pore diameter of 0.6 microns or less; (ii) optionally having macro-pores, wherein the macro-pores are pores on the active VPO catalyst that each have an individual pore diameter from above 0.6 microns to 10 microns; (iii) the micro-pore volume is at least 0.2 cc/g and comprises at least about 55% of the total pore volume; and (iv) the total pore volume is at least 0.27 cc/g.

Embodiments of the present invention disclose a process for preparing a VPO catalyst of the present invention that comprise the steps of: (i) selecting an active VPO catalyst; and (ii) contacting the active VPO catalyst with one or more fluids comprising an organic solvent.

Embodiments of the present invention disclose a process for preparing maleic anhydride comprising the step of reacting a hydrocarbon having at least four carbons in a straight chain with a molecular oxygen-containing gas in the presence of catalyst of the present invention.

Embodiments of the present invention disclose a process of making maleic anhydride using the catalyst of the present invention.

Embodiments of the present invention also disclose a process of increasing pore size in a catalyst by the steps of (i) selecting an active VPO catalyst; and (ii) contacting the active VPO catalyst with one or more fluids comprising an organic solvent.

The foregoing has outlined rather broadly the features of the present invention in order that the detailed description of the invention that follows may be better understood. Additional features and advantages of the invention will be described hereinafter that form the subject of the claims of the invention. It should be appreciated by those skilled in the art that the conception and the specific embodiments disclosed may be readily utilized as a basis for modifying or designing other structures for carrying out the same purposes of the present invention. It should also be realized by those skilled in the art that such equivalent constructions do not depart from the spirit and scope of the invention as set forth in the appended claims.

BRIEF DESCRIPTION OF THE DRAWINGS

So that the manner in which the above recited features of the present invention can be understood in detail, a more particular description of the invention, briefly summarized above, may be had by reference to embodiments, some of which are illustrated in the appended figures. It is to be noted, however, that the appended figures illustrate only typical embodiments of this invention and are therefore not to be considered limiting of its scope, for the invention may admit to other equally effective embodiments.

DETAILED DESCRIPTION OF THE INVENTION

Figure 1:
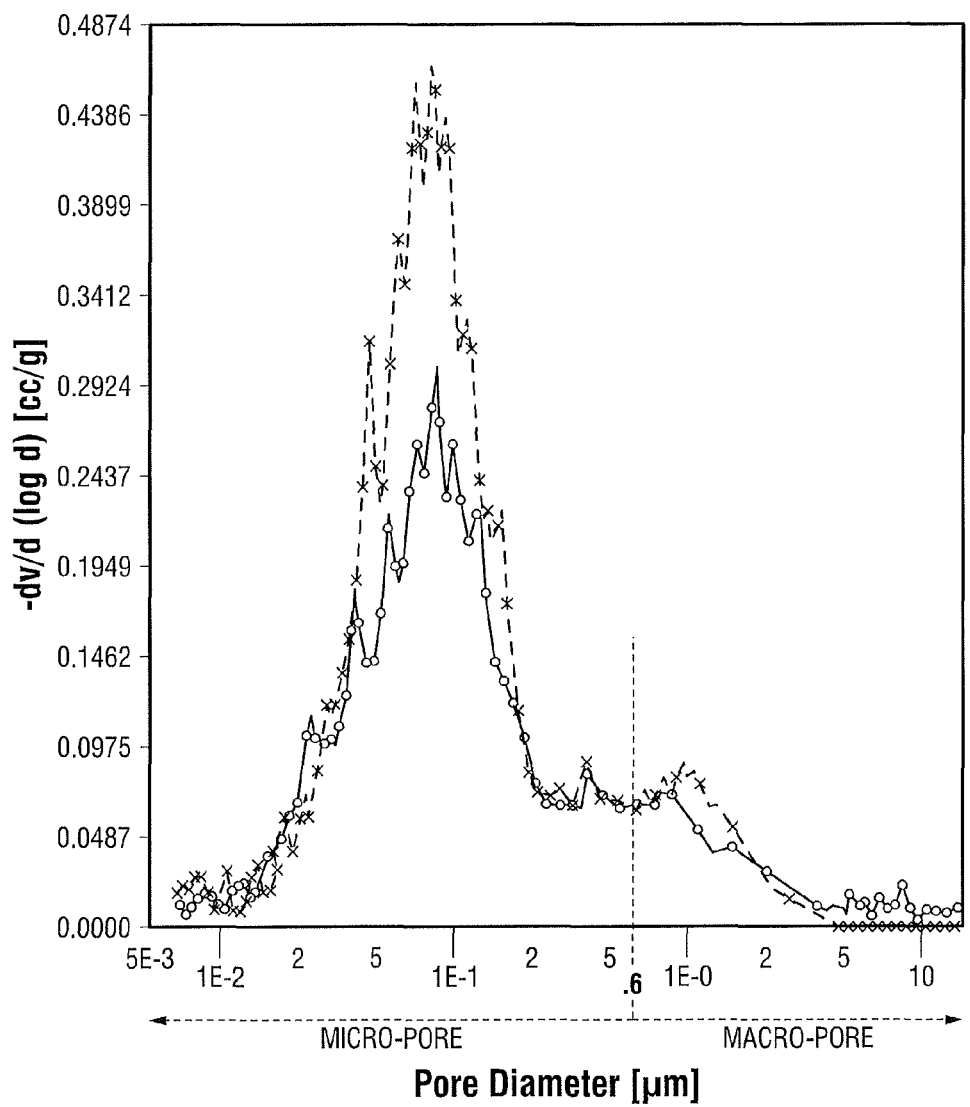
FIG. 1 illustrates the pore size distribution difference between the original catalyst and the catalyst of present invention.

It has now been surprisingly found a catalyst, and a method of making such a catalyst, that comprising vanadium, phosphorus and oxygen (herein referred to as "VPO catalyst") having an improved micro-pore structure that has improved catalytic performance in the preparation of carboxylic acid anhydrides, such as maleic anhydride. This method and result are novel and unexpected in view of the prior teachings which relate to VPO catalysts. Namely, one skilled in the art would not expect to be able to improve micro-pore structure given current pore building agents that generate new macro-pores.

As used herein, "calcination" generally embraces one or more gas and/or thermal treatment steps of a VPO catalyst precursor. The term "active" VPO catalyst thus refers to a catalyst that has been transformed from a VPO catalyst precursor by treatment with one or more gas and/or thermal treatment steps.

By the term "improved micro-pore structure", it is meant there is an improvement in at least one micro-structure property, which properties include, number of micro-pores, volumes of existing micro-pores, or total micro-pore volume.

By the term "improved catalyst performance" it is meant there is an improvement in at least one of the VPO catalyst properties, which properties include yield, selectivity, conversion; yield, selectivity or conversion performance over time, loading characteristics and operability. For purposes of this invention, the term "yield" means the ratio of the moles of maleic anhydride obtained to the moles of hydrocarbon feedstock introduced into a reactor multiplied by 100, the term expressed as mol %. The term "selectivity" means the ratio of moles of maleic anhydride obtained to the moles of hydrocarbon feedstock reacted or converted multiplied by 100, the term expressed as mol %. The term "conversion" means the ratio of moles of hydrocarbon feedstock reacted to the moles of hydrocarbon introduced into a reactor multiplied by 100, the term expressed as mol %.

Embodiments of the present invention disclose a catalyst for the catalytic oxidation of hydrocarbons to produce a carboxylic acid anhydride comprising an active VPO catalyst, wherein the active VPO catalyst is characterized by: (i) having a total pore volume, micro-pores and a micro-pore volume, wherein the micro-pores are pores on the active VPO catalyst that each have a pore diameter of 0.6 microns or less; (ii) optionally having macro-pores, wherein the macro-pores are pores on the active VPO catalyst that each have an individual pore diameter from above 0.6 microns to 10 microns; (iii) the micro-pore volume is at least 0.2 cc/g and comprises at least about 55% of the total pore volume; and (iv) the total pore volume is at least 0.27 cc/g.

The active VPO catalyst selected for this invention may be any kind of known active VPO catalyst used for organic selective oxidation, particularly maleic anhydride production. Broadly described, the active VPO catalyst is prepared by reacting a vanadium-containing compound and a phosphorus-containing compound in an alcoholic medium to produce a VPO catalyst precursor, and activating the VPO catalyst precursor by calcination to convert a substantial fraction of the precursor composition to vanadyl pyrophosphate $(VO)_2P_2O_7$. Thus, in one embodiment, the active VPO catalyst may be a material having at least 70% $(VO)_2P_2O_7$ by weight based on the weight of the catalyst. In another embodiment, the active VPO catalyst may be a material having at least 90% $(VO)_2P_2O_7$ by weight based on the weight of the catalyst. A commercial example of an active VPO catalyst suitable for use in the present invention is sold under the trade name MARS V by Huntsman Corporation (The Woodlands, Tex.).

Vanadium-containing compounds in general are those containing pentavalent vanadium and include vanadium pentoxide or vanadium salts, such as ammonium metavanadate, vanadium oxytrihalides, and vanadium alkylcarboxylates. Among these compounds, vanadium pentoxide is preferred.

Phosphorus-containing compounds are preferably those that contain pentavalent phosphorus. Suitable phosphorus-containing compounds include phosphoric acid, phosphorus pentoxide, or phosphorus perhalides such as phosphorus pentachloride. Of these phosphorus-containing compounds, phosphoric acid and phosphorus pentoxide are preferred.

Promoter elements optionally may be added as solids, suspension of solids, or solutions to the catalyst precursor slurry either prior to or after the reaction of the vanadium and phosphorus-containing compounds has taken place. Promoter compounds that may serve as sources of the promoter elements include metal halides, metal alkoxides, and metal carboxylates. Of these compounds, metal carboxylates are preferred. Suitable carboxylates for metal salts include formate, acetate, propionate, butyrate, isobutyrate, pentanoate, hexanoate, heptanoate, octanoate, nonanoate, decanoate, and 2-ethylhexanoate. Of these carboxylates, 2-ethylhexanoate is preferred. In an embodiment, the promoter elements include Zr, Zn, Ti, Mn, Bi, Sn, Co, Ni, Mo, Nb, Cr, Fe, or combinations thereof. The promoter may be less than 3.0% by weight of total catalyst weight.

The reaction between the vanadium and phosphorus-containing compounds may be carried out at any suitable temperature. In an embodiment, the reaction may be carried out at a temperature within a range of about 90° C. to about 120° C. and at a phosphorus/vanadium atom ratio (P/V) of 1.00 to 1.15.

During the course of carrying out the reaction, the VPO catalyst precursor forms and precipitates from the precursor slurry as a finely divided precipitate that may also contain the optional promoter elements. The VPO catalyst precursor may be recovered after cooling to below about 50° C. by conventional techniques well known to those skilled in the art, including filtration, centrifugation, and decantation.

The VPO catalyst precursor may then be dried at a relatively modest temperature of, for example, about 110° C. to about 150° C., and then subjected to "post dry" treatment (roasting) at a temperature in the range of about 200° C. to about 275° C.

The VPO catalyst precursor may then be directly converted to an active VPO catalyst by one or more gas and thermal treatments or it may first be compressed in a press or die to produce a slug and then subjected to gas and thermal treatment. The slug may be compressed into any desired shape or form, such as a cylinder, pyramid, cube, or sphere, to a measured density of between about 1.20 g/cm³ to about 1.70 g/cm³, preferably between about 1.40 g/cm³ to about 1.60 g/cm³. Binding and/or lubricating agents may be added, if desired, at amounts ranging from about 2% to about 6% by weight based on the total weight of the slug and may include starch, calcium stearate, stearic acid and graphite.

Converting the VPO catalyst precursor into the active VPO catalyst may take place in three controlled stages: (1) an initial heat-up stage, (2) a rapid heat-up stage, and (3) a maintenance/finishing stage.

In the initial heat-up stage, the VPO catalyst precursor is heated in an atmosphere selected from among air, steam, inert gas, and mixtures thereof, at any convenient heat-up rate. In general, suitable temperatures for the initial heat-up stage range from about 200° C. to about 300° C., alternatively a temperature from about 250° C. to about 275° C.

After the desired temperature has been achieved in the initial heat-up stage, the initially selected atmosphere (in the event it does not contain molecular oxygen and steam and/or has a different composition than that which is desired for the rapid heat-up stage) may be replaced by a molecular oxygen/steam-containing atmosphere, while maintaining the VPO catalyst precursor at the temperature achieved in the initial heat-up stage. Such atmosphere optionally may contain an inert gas and, as such, may be conveniently represented by the formula:

$$(O_2)_x(H_2O)_y(IG)_z$$

where IG is an inert gas and x, y, and z represent mole % (or volume %) of the $O_2$, $H_2O$, and IG components, respectively, in the molecular oxygen/steam-containing atmosphere; with x having a value greater than zero (0) mol %, but less than 100 mol %; y having a value greater than zero (0) mol %, but less than 100 mol %; and z having a value representing the balance of the molecular oxygen/steam-containing atmosphere. In an embodiment, the atmosphere may contain at least a portion of molecular oxygen and water (as steam). The presence of the inert gas in such atmosphere, as indicated by the formula, is optional. Nonlimiting examples of inert gases suitable for use in the molecular oxygen/steam-containing atmosphere include (molecular) nitrogen, helium, argon, and the like, with nitrogen generally being preferred.

Once the molecular oxygen/steam-containing atmosphere is provided, the VPO catalyst precursor is subjected to the rapid heat-up stage. In the rapid heat-up stage, the initial heat-up stage temperature may be increased at a programmed rate of from about 2° C. per minute (° C./min) to about 12° C./min, preferably from about 4° C./min to about 8° C./min, to a value effective to eliminate or remove the water of hydration. In general, a temperature from about 340° C. to about 450° C., alternatively at least about 350° C., alternatively from about 375° C. to about 425° C. is suitable.

Following the rapid heat-up stage, the VPO catalyst precursor is subjected to the maintenance/finishing stage. In the maintenance/finishing stage, the temperature may be adjusted to a value greater than 350° C. but less than 550° C., preferably from about 375° C. to about 450° C., most preferably from about 400° C. to about 425° C. The adjusted temperature is then maintained, first in the molecular oxygen/steam-containing atmosphere for a time effective to provide a vanadium oxidation state of from about +4.0 to about +4.5, and thereafter in a nonoxidizing, steam-containing atmosphere for a time effective to complete the VPO catalyst precursor to active VPO catalyst transformation. In a manner similar to the molecular oxygen/steam-containing atmosphere, the nonoxidizing, steam-containing atmosphere may also optionally contain an inert gas, with nitrogen generally being the preferred inert gas.

The active VPO catalyst may be in one or more different physical forms. In one embodiment, the active VPO catalyst is in the form of a powder having any particle size or particle sizes. In another embodiment, the active VPO catalyst is in the form of a shaped body. The shaped body may be any shape, including a cylinder, a cored cylinder, a sphere, a pellet, a trilobe, a quadrolobe, a bead, a ring, a tablet or an irregular shape. Examples of shaped bodies are described in U.S. Pat. No. 5,168,090, the contents of which are incorporated herein by reference. [0001]

The pore size inside of the active VPO catalyst shaped body may also be altered by a pore building agent as described in U.S. Pat. Nos. 5,773,382 and 5,275,996, the contents of which are incorporated herein by reference.

The active VPO catalyst of this invention has a total pore volume, micro-pores and a micro-pore volume and optionally macro-pores. Total pore volume refers to the combined pore volume of both the micro-pores and the macro-pores. Micro-pores are pores on the active VPO catalyst that each have a pore diameter of 0.6 microns or less. Micro-pore volume refers to the combined volume of the micro-pores. Macro-pores are optional on the active VPO catalyst, because they do not inherently exist on the active VPO catalyst, but are rather added through pore building agents during the catalyst's manufacture or post-treatment. Macro-pores each have an individual pore diameter from above 0.6 microns to 10 microns.

In an embodiment of the present invention, the micro-pore volume is at least 0.2 cc/g and comprises at least about 55% of the total pore volume and the total pore volume is at least 0.27 cc/g. In another embodiment, the micro-pore volume is at least 0.2 cc/g and comprises at least about 90% of total pore volume and wherein the total pore volume is at least 0.25 cc/g. In other embodiments, the micro-pore volume comprise at least 40% of total pore volume, preferably at least 50%.

Embodiments of the present invention have a Brunauer-Emmett-Teller (BET) surface area of at least about 20 $m^2/g$ and an average vanadium oxidation state of between about 3.8 and about 4.4, preferably between 3.9 and 4.25, a normalized apparent shaped body density of between about 1.0 g/cc and about 2.0 g/cc. Preferred embodiments of the present invention have a side crush strength of at least 4 pounds.

Embodiments of the present invention preferably have a pore size distribution plot having a first intensive peak that corresponds to the micro-pores and optionally a second intensive peak that corresponds to the macro-pores as can be seen in FIG. 1.

Embodiments of the present invention provides a process for preparing a VPO catalyst exhibiting improved catalyst performance which process comprises the steps of selecting an active VPO catalyst and contacting the active VPO catalyst with one or more fluids containing an organic solvent to form an active VPO catalyst having a micro-pore volume of at least 0.2 cc/g. The fluid may also comprise a mixture of organic solvents. Embodiments of the present invention also disclose a process for increasing pores in a VPO catalyst which comprises the steps of selecting an active VPO catalyst; and contacting the active VPO catalyst with one or more fluids comprising an organic solvent, wherein the pores have a diameter from about 0.01 microns to about 0.6 microns.

The process disclosed in this invention increase total pore volume of the present invention catalyst by at least 20% compared with that of the original catalyst. In the process the selected solvents remove some components of VPO catalyst out from inside of catalyst body, thus increase total pore volume. X-ray diffraction appears to indicate a crystalline change in the structure. This process also appears to modify vanadium oxidation state of the catalyst. Moreover, the micro-pores having diameter less than 0.6 microns has a pronounced impact and its total pore volume increase at least 10%, preferably 20% depending on the time length of contacting between the original catalyst and solvent.

For use in this invention, the active VPO catalyst is subjected to a series of contactings with one or more fluids. A series of contactings is herein understood to include a single contacting step and a combination of consecutive contacting steps which employ one or more fluids.

In accordance with this invention, the fluid comprises an organic solvent or mixture of organic solvents. In one embodiment, each organic solvent has a dielectric constant within a range of about 5 to about 55. In another embodiment, the organic solvents all have a dielectric constant within a range of about 10 to about 50. As used herein, the term "dielectric constant" is defined as a measure in the reduction of an electric field around a charged particle dissolved in the organic solvent, as compared to the electric field strength around the same particle in a vacuum. The dielectric constant thus is a measure of the polarity of the organic solvent. The higher the dielectric constant of a given solvent is, the lower the electrostatic forces, both attractive and repulsive, are between two ions dissolved in the solvent. For example, ions of opposite charge have a higher tendency to dissociate in a solvent with a high dielectric constant. In addition, the value of the dielectric constant depends on the temperature under which it is measured. Here, the dielectric constant of the organic solvent refers to the dielectric constant as measured at room temperature or a temperature of between 20° C. to 25° C.

Examples of organic solvents suitable for use include, but are not limited to, methanol, ethanol, n-propanol, n-butanol, isopropanol, isobutanol, acetonitrile, acetone, methyl ethyl ketone, DMF(N,N-dimethylformamide), Dimethyl sulfoxide, tetrafuran, ethylene glycol, propylene glycol, diethylene glycol, dipropylene glycol, 1,4-butanediol, glycerin and a mixture thereof.

Eligibly, the fluid comprises for the greater part the organic solvent or mixture of organic solvents. Thus, the organic solvent content of the fluid in one embodiment is preferably at least 90% by weight, more preferably at least 95% by weight, even more preferably at least 99% by weight, in particular, at least 99.9% by weight, and more in particular at least 99.99% by weight relative to the weight of the fluid. In one embodiment, the fluid consists of an organic solvent or a mixture organic solvents.

In another embodiment, the fluid may further comprise relative small quantities of other components, including, but not limited to, water, other organic matter, or inorganic matter.

The extent and type of contacting may be carried out in a continuous fashion or it may be carried out in a batch type of operation. There may be one contacting, but the number of contactings may also be two or three or more, for example up to five or ten. The contacting of the active VPO catalyst may be static or slow motion relative to the fluid(s). Thus, in one embodiment, the active VPO catalyst is kept static and the fluid is moved relative to the catalyst or vice versa. The relative motion speed may be at any range to allow the organic solvent in the fluid to diffuse into the active VPO catalyst body, but not at a speed which substantially damages the catalyst's pre-shaped body.

The quantity of fluid used in the contactings relative to the quantity of active VPO catalyst may be enough to cover the active VPO catalyst. The contacting may be carried out at any suitable temperature range, preferably within a range from room temperature (i.e. 20°-25° C.) to about 100° C. above the boiling point of the fluid, and more preferably from room temperature to the boiling point of the fluid. The contacting may be conducted in any pressure range, preferably from atmospheric pressure to 5 bars, more preferably from atmospheric pressure to 3 bars and most preferably at around 2 bars.

Contacting time may vary depending on the treatment conditions. The contacting time may be from a few minutes to a few weeks, whatever time is necessary to reach desired improved catalyst performance and as long as economic feasible. Thus, in one embodiment, the contacting time may range from a period of about 5 minutes to about 2 days. In another embodiment, the contacting time may range from a period of about 0.5 hours to about 12 hours.

After contacting the VPO catalyst, it may be desirable to perform a drying step. Drying of the contacted VPO catalyst may be performed at a certain temperature range under certain atmosphere. In one embodiment, drying may be carried out at a temperature ranging from about room temperature (i.e. 20° C. to 25° C.) to a temperature sufficient to remove the fluid from the VPO catalyst, for example, 300° C. In another embodiment, the temperature to remove the fluid from the VPO catalyst may be about 200° C. The temperature during drying may be held constant or varied over time. The drying may be carried out under a pressure range from about atmospheric pressure to vacuum with 10 mbar or with 50 mbar. The atmosphere may comprise air or inert gases or a mixture of air and inert gases. The inert gases may include nitrogen, helium, argon, carbon oxides, and mixtures thereof. In one embodiment, the atmosphere comprises air or nitrogen or a mixture thereof. The length of time of the drying step may vary from about 0.1 hour to a week or from about 0.5 hours to 3 days, or from about 1 hour to 12 hours depending on drying conditions.

The present invention also provides a process for preparing maleic anhydride which process comprises reacting a hydrocarbon having at least four (4) carbons in a straight chain or cyclic ring with a molecular oxygen-containing gas in the presence of the VPO catalyst having a micro-pore volume of at least 0.2 cc/g. The process may be carried out as a batch process; however, it is more suitable to carry out the process as a continuous process. In one embodiment, the process is a gas phase process, wherein a gaseous feed comprising the reactants is contacted with the solid VPO catalyst. The solid VPO catalyst may be present in the form of a packed or fixed bed or in the form of a fluidized bed of catalyst particles. According to one embodiment, the VPO catalyst may be used in a fixed-bed reactor having a shaped body described above. In another embodiment, the VPO catalyst may be used in a fluid-bed or transport-bed reactor using comminuted catalyst particles having a particle size of less than about 300 microns.

In yet another embodiment, the VPO catalysts are used in tube-shell fixed-bed (tubular) with heat exchanger-type reactors. The tubes of such reactors may be constructed of iron, stainless steel, carbon steel, nickel, and/or glass and may vary in diameter from about 0.635 cm (0.25 inch) to about 5.08 cm (2 inches) and in length from about 15.24 cm (6 inches) to about 762 cm (25 feet) or more. It is desirable to have the surfaces of the reactors at relatively constant temperatures, and some medium to conduct heat from the reactors. Without being limited by theory, such medium aids in temperature control. Non-limiting examples of such media include Woods metal, molten sulfur, mercury, molten lead, and eutectic salt baths. A metal block reactor whereby the metal surrounding the tube acts as a temperature regulating body may also be used.

The hydrocarbon having at least four carbons in a straight chain or cyclic ring as used herein refers to a hydrocarbon containing not less than four carbon atoms in either a straight chain or in a cyclic ring. The hydrocarbon may be saturated, unsaturated, cyclic or aromatic. As an example, the saturated hydrocarbon n-butane is satisfactory, but iso-butane (2-methylpropane) is not satisfactory for conversion to maleic anhydride although its presence is not harmful. Typically, the hydrocarbon contains four to ten carbon atoms. Thus, in addition to n-butane, other suitable saturated hydrocarbons include the pentanes, the hexanes, the heptanes, the octanes, the nonanes, the decanes, and mixtures of any of these, with or without n-butane, so long as a hydrocarbon having at least four carbon atoms in a straight chain is present in the saturated hydrocarbon molecule.

The hydrocarbon having at least four carbons in a straight chain also includes unsaturated hydrocarbons. Unsaturated hydrocarbons suitable for use include the butenes such as 1-butene and 2-butene, 1,3-butadiene, the pentenes, the hexenes, the heptenes, the octenes, the nonenes, the decenes, and mixtures of any of these, with or without the butenes, again, so long as the requisite hydrocarbon chain having at least four carbon atoms in a straight chain is present in the molecule.

In another embodiment, the hydrocarbon having at least four carbons in a cyclic ring is a cyclic hydrocarbon, for example, cyclopentane and cyclopentene, or an aromatic hydrocarbon, such as benzene.

Preferably, the hydrocarbon having at least four carbons in a straight chain or cyclic ring is selected from n-butane as the saturated hydrocarbon, 1-butene or 2-butene as the unsaturated hydrocarbons, and benzene as the aromatic hydrocarbons, with n-butane being most preferred of all feedstocks. It will be noted that the aforementioned feedstocks may not be pure substances but may be technical grade hydrocarbons. Moreover, a mixture of hydrocarbons having at least four carbon atoms in a straight chain or cyclic ring may also be used.

The reaction to convert the hydrocarbons to maleic anhydride may include contacting the hydrocarbons having at least four carbons in a straight chain or in a cyclic ring admixed with a molecular oxygen-containing gas (including molecular oxygen), such as air, synthetic air, molecular oxygen-enriched air, or "pure" oxygen (i.e. oxygen originating from air fractionation) with the VPO catalyst at elevated temperatures. In addition to the hydrocarbon and molecular oxygen-containing gas, other gases such as nitrogen and steam may be present or added to the reactant feed stream. In an embodiment, the hydrocarbon may be admixed with the molecular oxygen-containing gas, preferably air, at a concentration of from about one (1) mole percent to about ten (10) mole percent hydrocarbon and contacted with the VPO catalyst at a space velocity of about 100 $hr^{-1}$ to about 4,000 $hr^{-1}$ at a temperature between about 300° C. and about 600° C., preferably 1,000 hr$^{-1}$ to 3,000 hr$^{-1}$ and about 325° C. to about 450° C., to provide an excellent yield and selectivity to maleic anhydride.

The reaction may be conducted at atmospheric, super atmospheric, or subatmospheric pressure. In an embodiment, the reaction may be conducted at or near atmospheric pressure. Generally, pressures of from about 1.013×10$^{-2}$ kPa-gauge (14.7 psig, 1 atmosphere) to about 3.45×10$^{-2}$ kPa-gauge (50 psig) may be conveniently employed.

In an embodiment, the principal product from the oxidation of the aforementioned suitable feedstock is maleic anhydride, although small amounts of citraconic anhydride (methyl maleic anhydride) may also be produced when the feedstock is a hydrocarbon containing more than four carbon atoms. The maleic anhydride produced by using the VPO catalysts may be recovered by any suitable means. For example, maleic anhydride may be recovered by direct condensation or by absorption in suitable media with subsequent separation and purification of the maleic anhydride.

The recovered maleic anhydride may then be used in a variety of applications, for example, as a chemical intermediate in the synthesis of fumaric and tartaric acid and in certain agrochemical chemicals, dye intermediates and pharmaceuticals. It may also be used as a co-monomer for polyester and alkyd resins, as an ingredient in the manufacture of surface coatings, lubricant additives, plasticizers and as a preservative in oils and fats.

Embodiments of the present invention also disclose maleic anhydride produced by the process of reacting a hydrocarbon having at least four carbons in a straight chain with a molecular oxygen-containing gas in the presence of an active VPO catalyst, wherein the active VPO catalyst has a total pore volume, micro-pores and a micro-pore volume, wherein the micro-pores are pores on the active VPO catalyst that each have a pore diameter of 0.6 microns or less. The active VPO catalyst optionally has macro-pores, wherein the macro-pores are pores on the active VPO catalyst that each have an individual pore diameter from above 0.6 microns to 10 microns. The active VPO catalyst has a micro-pore volume that is at least 0.2 cc/g and comprises at least about 55% of the total pore volume; and the total pore volume is at least 0.27 cc/g.

It is apparent that certain features of the invention, which are for clarity described herein in the context of separate embodiments, may also be provided in combination in a single embodiment. Conversely, features of the invention which are described in the context of a single embodiment may also be provided separately or in any suitable sub-combination.

The following specific examples illustrating the best currently-known method of practicing this invention are described in detail in order to facilitate a clear understanding of the invention. It should be understood, however, that the detailed expositions of the application of the invention, while indicating preferred embodiments, are given by way of illustration only and are not to be construed as limiting the invention since various changes and modifications within the spirit of the invention will become apparent to those skilled in the art from this detailed description.

To further illustrate various illustrative embodiments of the present invention, the following non-limiting examples are provided.

EXAMPLES

Original Catalyst Preparation in General

The following catalyst preparation process demonstrates the use of traditional pore builder agent to create macro-pores. A round bottom flask with a paddle stirrer, a thermometer, a heating mantle, and a reflux condenser, was charged with 6788 g of isobutyl alcohol, 786 grams of V2O5 and 346 grams of oxalic acid dihydrate, to which was added 927 grams of 105.0% H3PO4. The resulting mixture was then refluxed for about 16 hours to give a bright blue mixture. After distilled off 1739 grams of isobutyl alcohol, the mixture was cooled and 50% of the remaining isobutyl alcohol was decanted away to produce concentrated slurry, and then the slurry was transferred to a tray and dried between 110° C. and 150° C. for 24 hours under vacuum. The dried material was then further dried by heating in air at 250-260° C. for several hours to further remove organic residue and yield a grey-black catalyst precursor powder.

The catalyst precursor was blended well with a stearic acid as pore builder and graphite as lubricant for tableting. The blend contained about 10 wt. % of stearic acid and 4 wt. % graphite, and were individually made into 12.7 mm diameter cylinderical slugs with a table density of 1.3 to 1.4 g/cc using a Stokes 512 Rotary Tableting machine. These slugs were granulated to less than 1 millimeter (mm) particles to produce the dense powder which was tabletted into 6.35 mm diameter cylinders having three equidistant spaced grooves etched in the longitudinal surface thereof.

The tablets were then loaded into an oven to remove stearic acid and create some macro-pores. The oven was ramped up from room temperature to 175° C., 185° C. and 198° C. step by step and held each step for 5.5 h, finally ramped up to 250° C. and held for 1.5 h and then cooled down. During the removal of stearic acid, air flew constantly at about 10 liter/min.

After removal of pore builder, the catalyst precursor underwent activation, in which tablets were loaded into trays in an oven. Tablets was heated up to 260° C. under air purge and held for an hour, next heated up to 405° C. and held for 30 minutes with purge of air and nitrogen mixture (55% nitrogen in volume), then heated up to 425° C. and held for two hours, finally kept temperature at 425° C. unchanged for another 6 h, but during this 6 hours the atmosphere was changed into nitrogen and steam by 50/50 in volume. After cooled down, the activated catalyst thus obtained is called original catalyst.

For the following examples, pore volume and pore size distribution was measured by standard mercury intrusion porosimetry, which was carried out in Quantachrome poremaster, and surface area by the Brunauer-Emmett-Teller (BET) method.

Comparative Example 1

Example 1 compares the pore size distribution and normalized pore volume of an original (untreated) catalyst to an active VPO catalyst of the present invention. The original catalyst used in this example was collected from one batch of catalyst with a brand name of MARS V which is commercially available from Huntsman Corporation.

To make the active VPO catalyst of the present invention, about 100 g of this catalyst was loaded into a basket made of gauze and immersed the basket completely into a thermal bath with propylene glycol (≥99.5%, Sigma-Aldrich) at about 100° C. without stirring. After about an hour soaking, the temperature of the thermal bath dropped to about 90° C., then the basket was taken out and reheated the thermal bath back to 100° C., then put the basket back into the bath again for soaking. After another hour soaking, the basket was taken out from the bath and reheated the bath and put the basket with catalyst back to hot bath again. This procedure was repeated for 4 times. So this catalyst was accumulatively treated in solvent for 4 hours.

Wet catalysts were then put into a preheated oven at 100° C. with nitrogen purge. After dried at 100° C. for one hour, the catalysts were heated up to 180° C. and hold there for 3 h, then ramped up to 250° C. and held there for 3 h, finally cooled down to room. The catalysts thus obtained after contacted with solvent are the catalysts of the present invention.

FIG. 1 shows the pore size distribution difference between the original (untreated) catalyst and the catalyst of present invention (after contacting with solvent). It clearly indicates that the population of the pores having diameter from 0.01 microns to 0.6 microns has been significantly increased, while the pore having diameter bigger than 0.6 microns also increased to certain extent.

Figure 2:
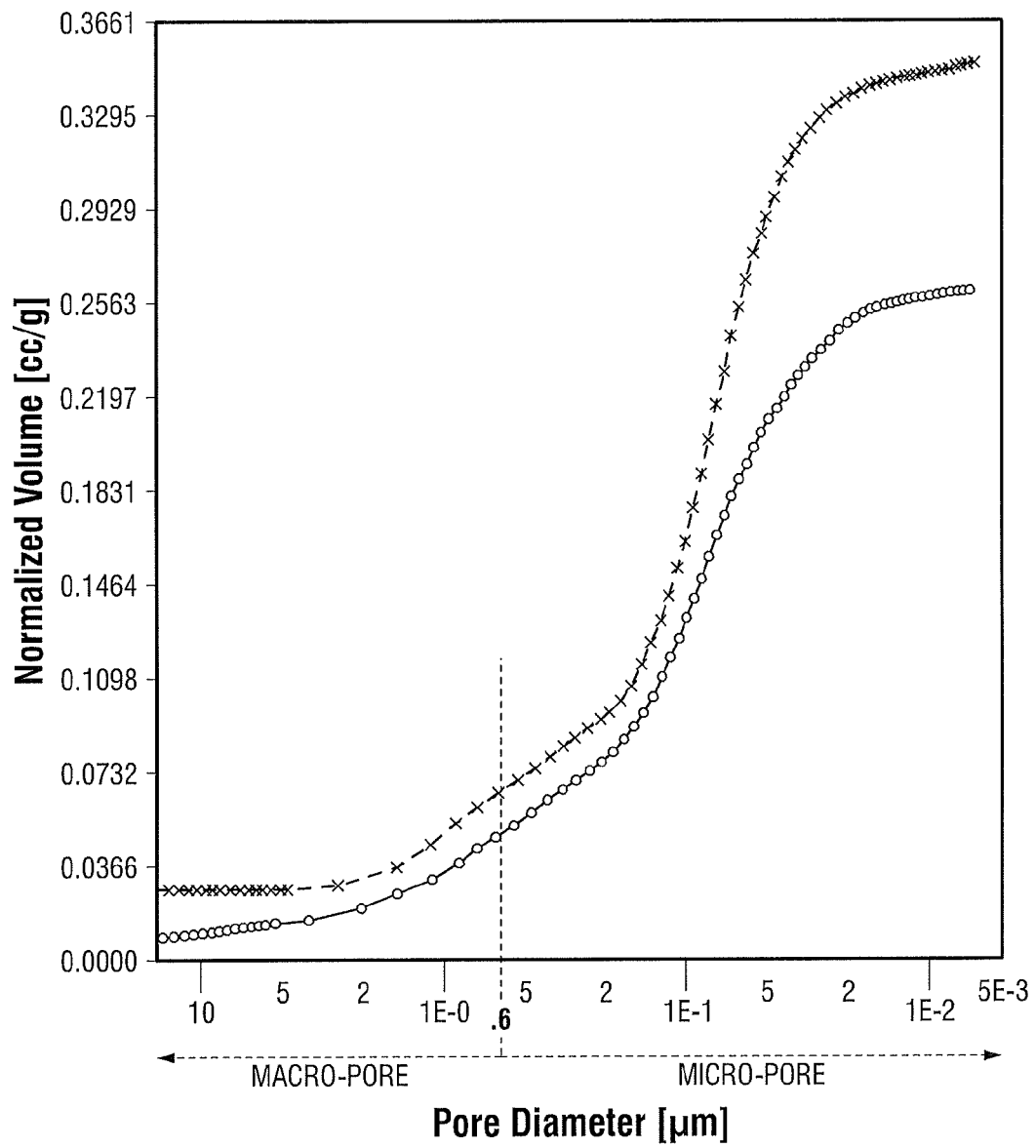
FIG. 2 illustrates the normalized pore volume vs. pore size of the original catalyst and the catalyst of present invention.

FIG. 2 shows the normalized pore volume vs. pore size of the original catalyst and the catalyst of present invention. It clearly shows the total pore volume has been greatly increased after contacting with solvent. The total pore volume difference (having pore diameter larger than 0.006 microns) is (0.3487-0.2606)=0.0881 cm$^3$/g, while the pore volume difference having pore diameter larger than 0.6 microns is (0.0610-0.0440)=0.017 cm$^3$/g. So the pore volume difference having pore diameter less than 0.6 microns is (0.0881-0.017)=0.0711 cm$^3$/g. In another words, the pore volume having pore diameter less than 0.6 microns has increased 0.0711 cm$^3$/g. The original catalyst have pore volume of pore having diameter less than 0.6 microns is (0.2606-0.044)=0.2166 cm$^3$/g. So percentage wise the pore volume having pore diameter less than 0.6 microns has increase 0.0771/0.2166=32.8%. Total pore volume increases 0.0881/0.2606=33.8%.

Standard micro-reactor test showed the original catalyst had maleic anhydride yield of about 56.8%, while the catalyst of the present invention (after contacting with solvent) had 58.9%. The catalyst of the present invention has established 2.1 yield point improvement compared to the original catalyst. Catalyst performance improvement reflected the pore volume increase.

Comparative Examples 2-6

These examples compare a sample catalyst that has been treated with traditional pore builder agent versus five active VPO catalysts of the present invention.

Preparation of Examples 2-6 of the Present Invention

An original catalyst prepared in similar way described in "Original Catalyst Preparation In General," except that the shape of the tablet has been modified to a round trilobe and the weight per tablet is reduced about 8%. This particular original catalyst has total pore volume of 0.2656 cm$^2$/g and BET surface area of 18.09 m$^2$/g. It was divided into five portions. Each portion of the catalyst was treated in propylene glycol (≥99.5%, Sigma-Aldrich) as described in Example 1 for 4 hours.

Figure 3:
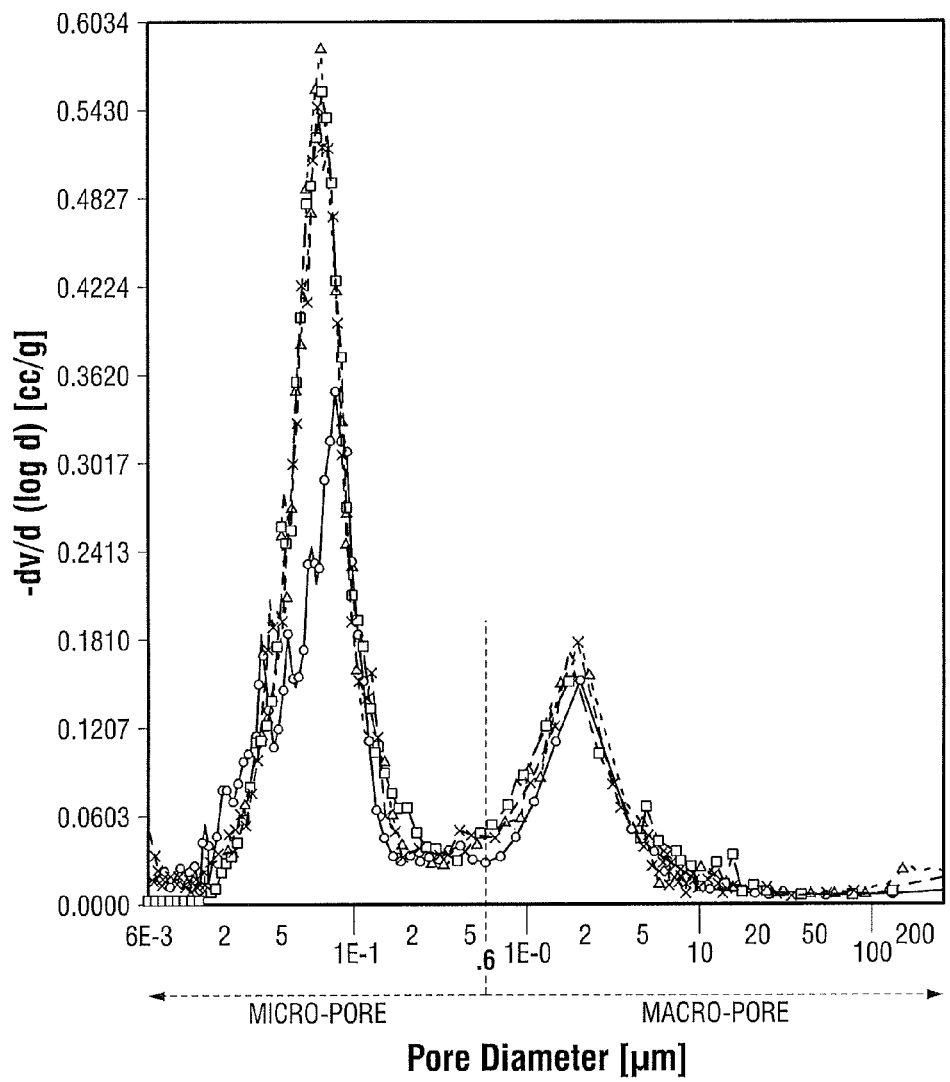
FIG. 3 illustrates the pore size distribution difference between the original catalyst that has been treated with additional traditional pore builder agent versus three active VPO catalysts of the present invention.
Figure 4:
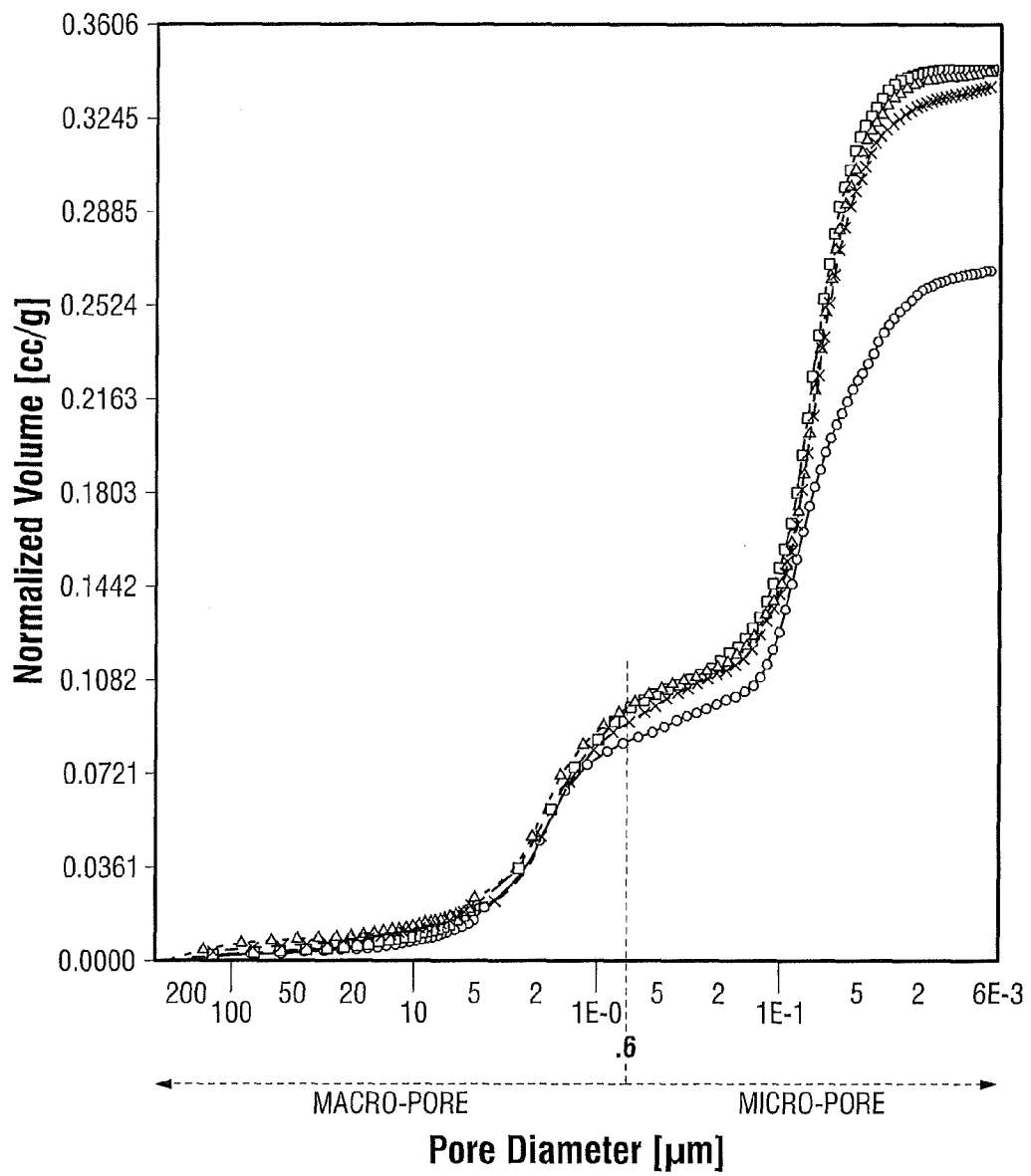
FIG. 4 illustrates the normalized pore volume vs. pore size of the original catalyst that has been treated with additional traditional pore builder agent versus three active VPO catalysts of the present invention.

These catalysts were analyzed by BET surface area, pore size distribution and catalytic performance. FIGS. 3 and 4 show pore size distribution and normalized pore volume, respectively. Table 1 shows the original catalyst treated with traditional pore builder and all five treated catalysts in BET surface area, pore volume and pore size distribution. It is clear that the BET surface area increased significantly ranging from 68-93% depending on the particular catalyst. Total pore volume increased about 22-40% after contacting selected solvent. The pore volume of the pore having diameter less than 0.6 microns has increased about 30-40%. The catalyst of the present invention has more than 66% of pore volume having pore diameter less than 0.6 microns.

TABLE 1 comparison of original catalyst and the catalyst after contacted with propylene glycol.

| Catalyst | BET (m2/g) | Total pore volume (cc/g) | Total Vp increase (%) | Vp of <0.6 microns | Vp % of <0.6 microns | Increase Vp % of <0.6 microns |
|---|---|---|---|---|---|---|
| Original treated w/ pore builder | 18.09 | 0.2656 | 0.0 | 0.1765 | 66.45 | 0.0 |
| Example 2 | 30.75 | 0.3370 | 26.9 | 0.2394 | 71.04 | 35.6 |
| Example 3 | 32.62 | 0.3424 | 28.9 | 0.2383 | 69.60 | 35.0 |
| Example 4 | 33.60 | 0.3434 | 29.3 | 0.2364 | 68.84 | 33.9 |
| Example 5 | 33.06 | 0.3697 | 39.2 | 0.2487 | 67.27 | 40.9 |
| Example 6 | 34.94 | 0.3264 | 22.9 | 0.2308 | 70.71 | 30.8 |

Example 7

Figure 5:
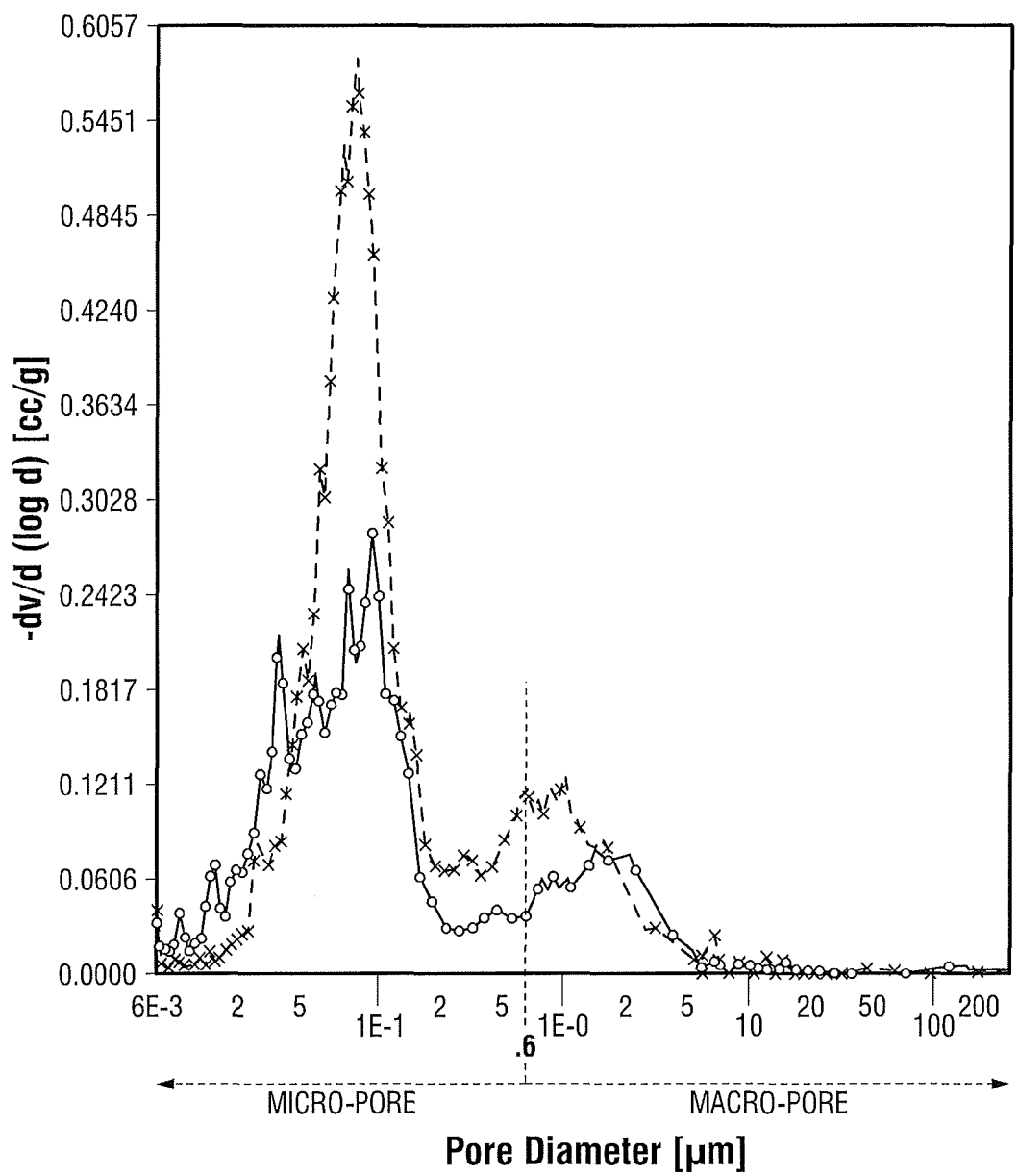
FIG. 5 illustrates another pore size distribution of original catalyst and the catalyst of this invention for Example 7.
Figure 6:
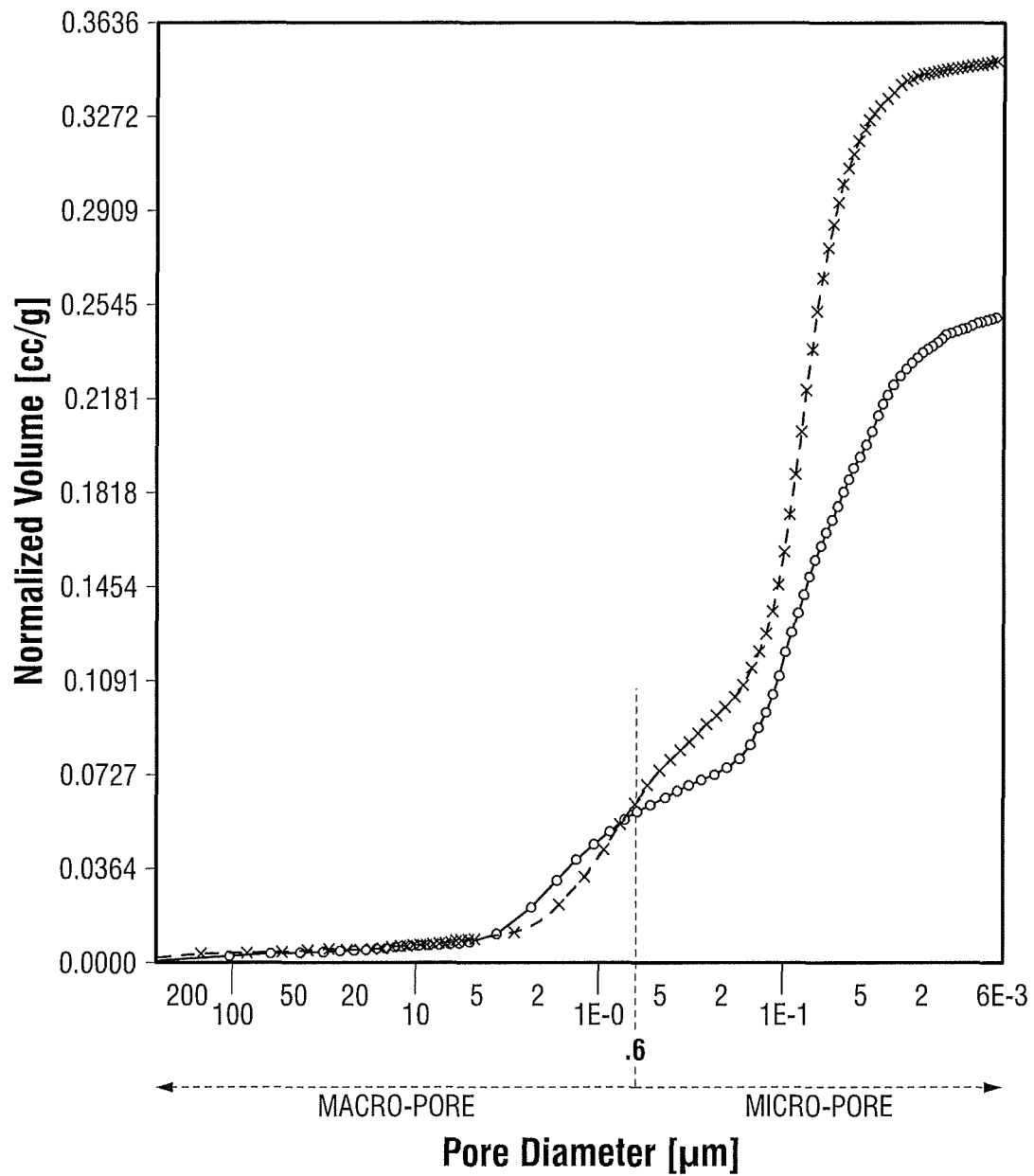
FIG. 6 illustrates the normalized pore volume vs. pore size of the original catalyst and the catalyst of present invention for Example 7.

An original (untreated) catalyst was prepared in the same way as described in "Original Catalyst Preparation In General." A catalyst of the present invention was made by taking the original (untreated) catalyst and allowing it to contact ethylene glycol (≥99.5%, Sigma-Aldrich) at about 100° C. for 4 hr without stirring. Wet catalysts were put into a preheated oven at 100° C. with nitrogen purge. After dried at 100° C. for one hour, the catalysts were heated up to 190° C. and hold there for 3 hr, then ramped up to 250° C. and held there for 3 hr, finally cooled down to room. FIGS. 5 and 6 show pore size distribution and normalized pore volume, respectively. Based on these two plots, various pore volumes and their changes by contacting solvent have been calculated in a way described in Example 1 and tabulated in Table 2. It is clear that total pore volume increase about 40% and the small pore having pore diameter less than 0.6 microns increased 51%.

TABLE 2 comparison of original catalyst and the catalyst after contacted with ethylene glycol.

| Catalyst | BET (m2/g) | Total pore volume (cc/g) | Vp increase (%) | Vp of <0.6 microns | Vp % of <0.6 microns | Increase Vp % of <0.6 microns |
|---|---|---|---|---|---|---|
| Original catalyst for example 7 | 14.15 | 0.2473 | 0 | 0.18542 | 75.0 | 0 |
| Example 7 of the present invention | 24.6 | 0.3463 | 40.03 | 0.28088 | 81.1 | 51.5 |

Example 8

Figure 7:
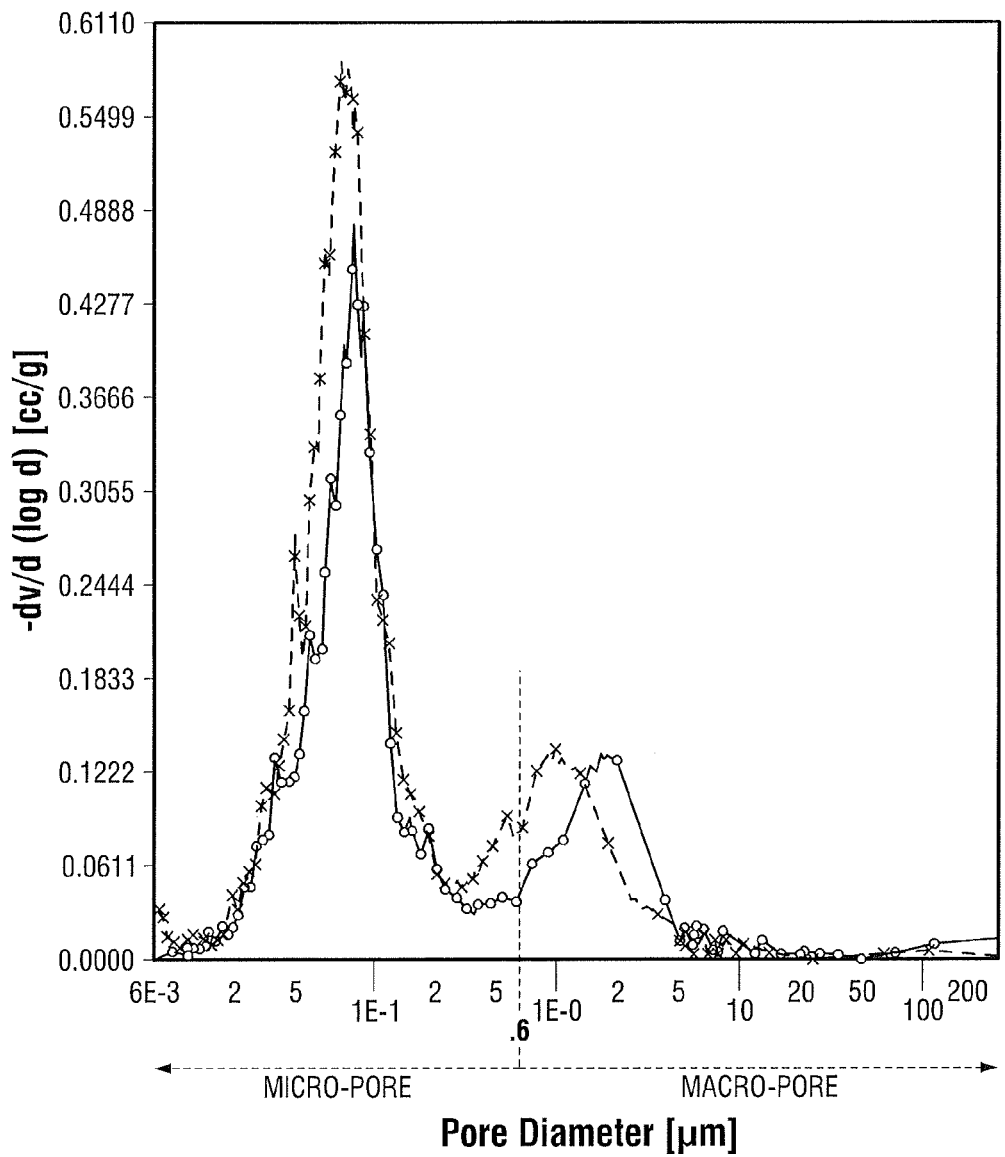
FIG. 7 illustrates another pore size distribution of original catalyst and the catalyst of this invention for Example 8.
Figure 8:
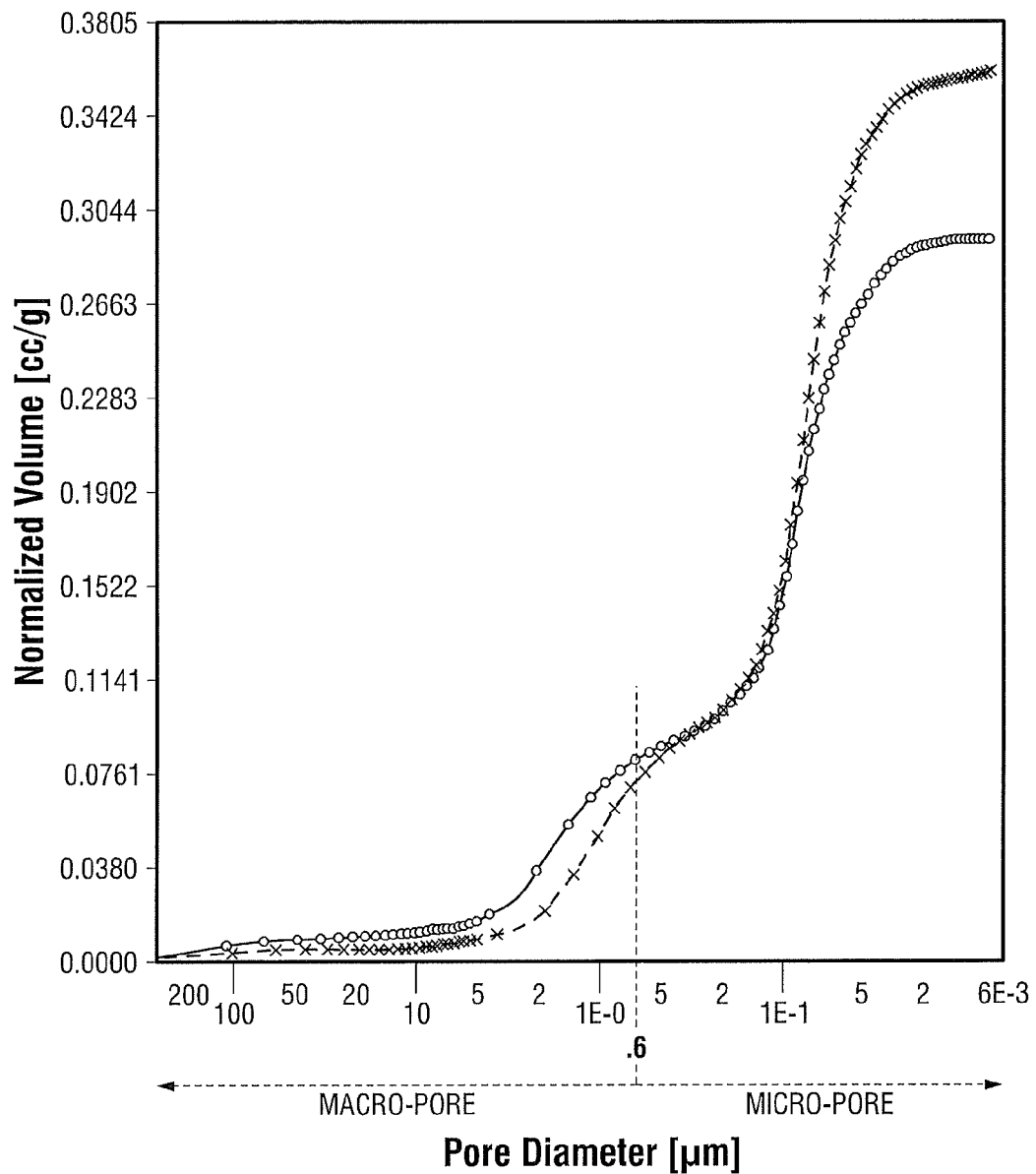
FIG. 8 illustrates the normalized pore volume vs. pore size of the original catalyst and the catalyst of present invention for Example 8.

An original catalyst was prepared in the same way as described in "Original Catalyst Preparation In General." A catalyst of the present invention was made by taking the original (untreated) catalyst and allowing it to contact propylene glycol (≥99.5%, Sigma-Aldrich) at about 100° C. for 6 hr without stirring. Wet catalysts were put into a preheated oven at 100° C. with nitrogen purge. After dried at 100° C. for one hour, the catalysts were heated up to 180° C. and hold there for 3 hr, then ramped up to 250° C. and held there for 3 hr, finally cooled down to room. FIGS. 7 and 8 show pore size distribution and normalized pore volume, respectively. Table 3 shows the original catalyst and the treated catalysts in BET surface area, pore volume and pore size distribution.

TABLE 3 comparison of original catalyst and the catalyst after contacted with propylene glycol.

| Catalyst | BET (m2/g) | Total pore volume (cc/g) | Vp increase (%) | Vp of <0.6 microns | Vp % of <0.6 microns | Vp % of <0.6 microns |
|---|---|---|---|---|---|---|
| Original catalyst for example 8 | 19.73 | 0.2933 | 0 | 0.2248 | 76.6 | 0.0 |
| Example 8 of the present invention | 35.98 | 0.3624 | 23.56 | 0.2787 | 76.9 | 24.0 |

Examples 9-10

Figure 9:
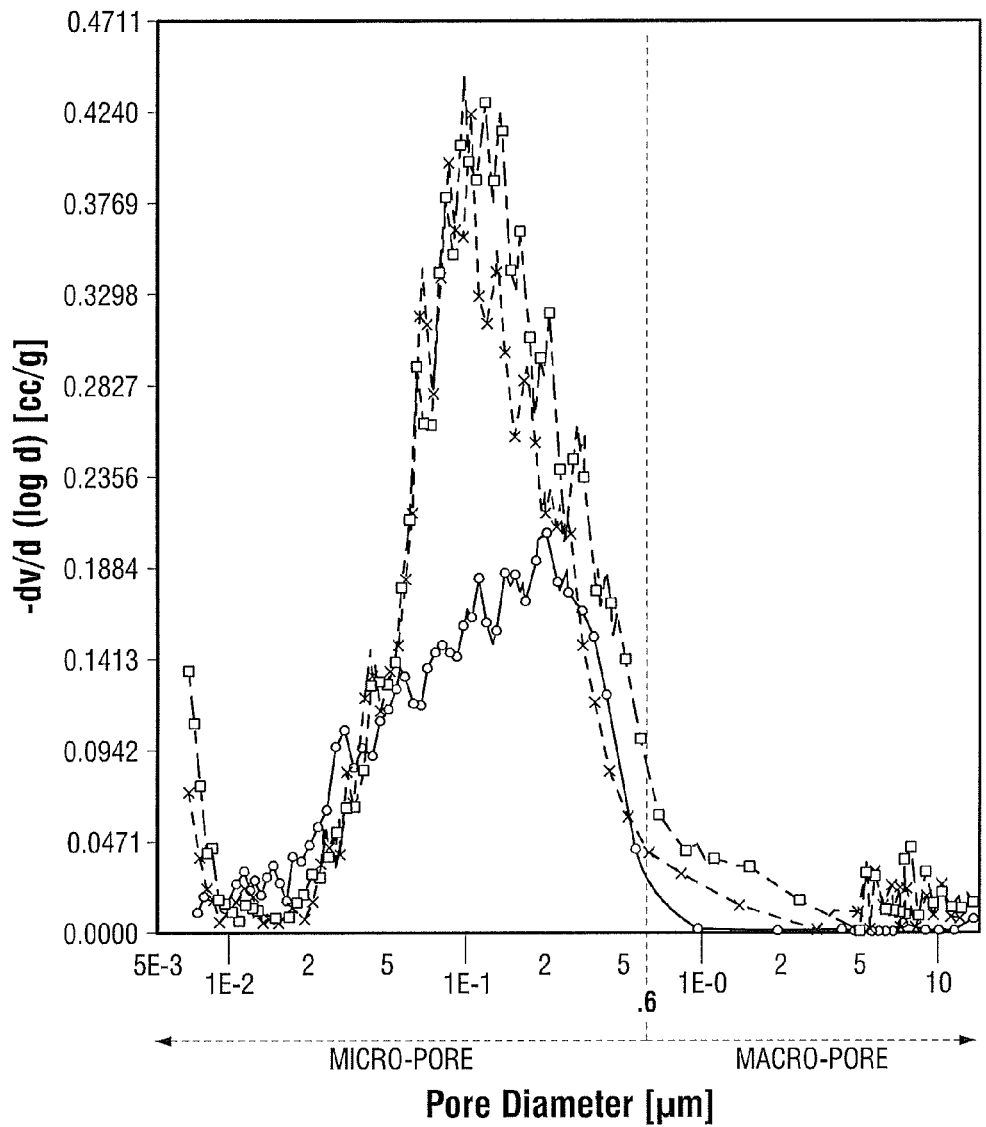
FIG. 9 illustrates another pore size distribution of untreated catalyst and the catalyst of this invention for Examples 9 and 10.

An original catalyst used in this example was collected from one batch of commercial catalyst with a brand name of MARS IV from Huntsman Corp. MARS IV catalyst is different from MARS V catalyst described in "Original Catalyst Preparation In General." MARS IV was manufactured without using any pore builder, whereas the MARS V was manufactured using pore builder. This is why MARS V catalyst has a group of big pores having pore diameter ranging from 0.6 to 10 microns, and MARS IV catalyst hasn't this group of big pores and only has a group of pores having diameter about 0.02 to 0.6 microns. This difference can be seen in pore size distribution plot. FIG. 9 shows MARS IV catalyst pore size distribution, only having one intensive peak for the pores having pore diameter around 0.02 to 0.6 microns.

The original catalyst of MARS IV was divided into two portions. About 100 g of each portion was contacted with propylene glycol (≥99.5%, Sigma-Aldrich) in a thermal bath as described in Example 1 for different length of time period. The catalyst was treated for 3 hr (Example 9) and the one was treated for 5 hr (Example 10).

Figure 10:
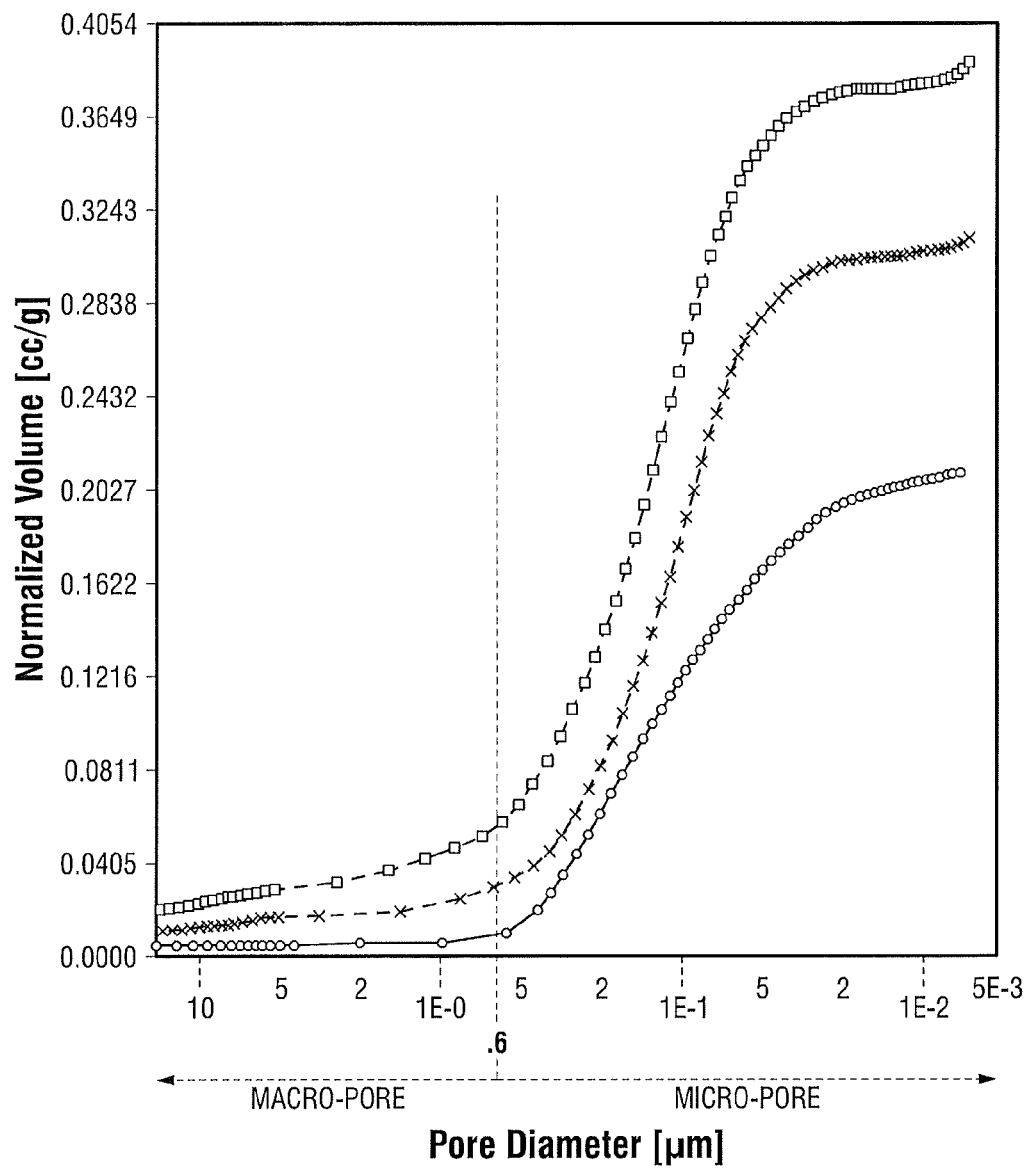
FIG. 10 illustrates the normalized pore volume vs. pore size of the untreated catalyst and the catalyst of present invention for Examples 9 and 10.

FIG. 9 shows that after contacted with solvent the peak intensity greatly increased compared to the original catalyst, indicating the population of the pores with pore diameter of about 0.02 to 0.6 microns has been increased. FIG. 10 further clearly shows the pore volume increase and detailed data is tabulated in Table 4.

TABLE 4

| Catalyst | BET (m2/g) | Total pore volume (cc/g) | Vp increase (%) | Vp of <0.6 microns | Vp % of <0.6 microns | Increase Vp % of <0.6 microns |
|---|---|---|---|---|---|---|
| Original for example 9-10 | 14.08 | 0.2076 | 0 | 0.1975 | 95.1 | 0 |
| Example 9 | 29.46 | 0.3096 | 49.1 | 0.2792 | 90.2 | 41.4 |
| Example 10 | 32.53 | 0.3861 | 86.0 | 0.3321 | 86.0 | 68.2 |

Comparative Example 11-13

This example demonstrates original catalyst preparation without using pore builder. The catalyst precursor was prepared in the same way as described in "Original Catalyst Preparation In General." After dried at 250-260° C. to remove alcohol residue, the precursor was blended with graphite only and without pore builder such as stearic acid. The blend containing about 4 wt. % graphite then underwent slugging and tableting as described in "Original Catalyst Preparation In General." As this type of tablet didn't contain any pore builder, it was not necessary to calcine the tablet, and the tablet was directly activated under air, nitrogen and steam as described in "Original Catalyst Preparation In General."

Figure 11:
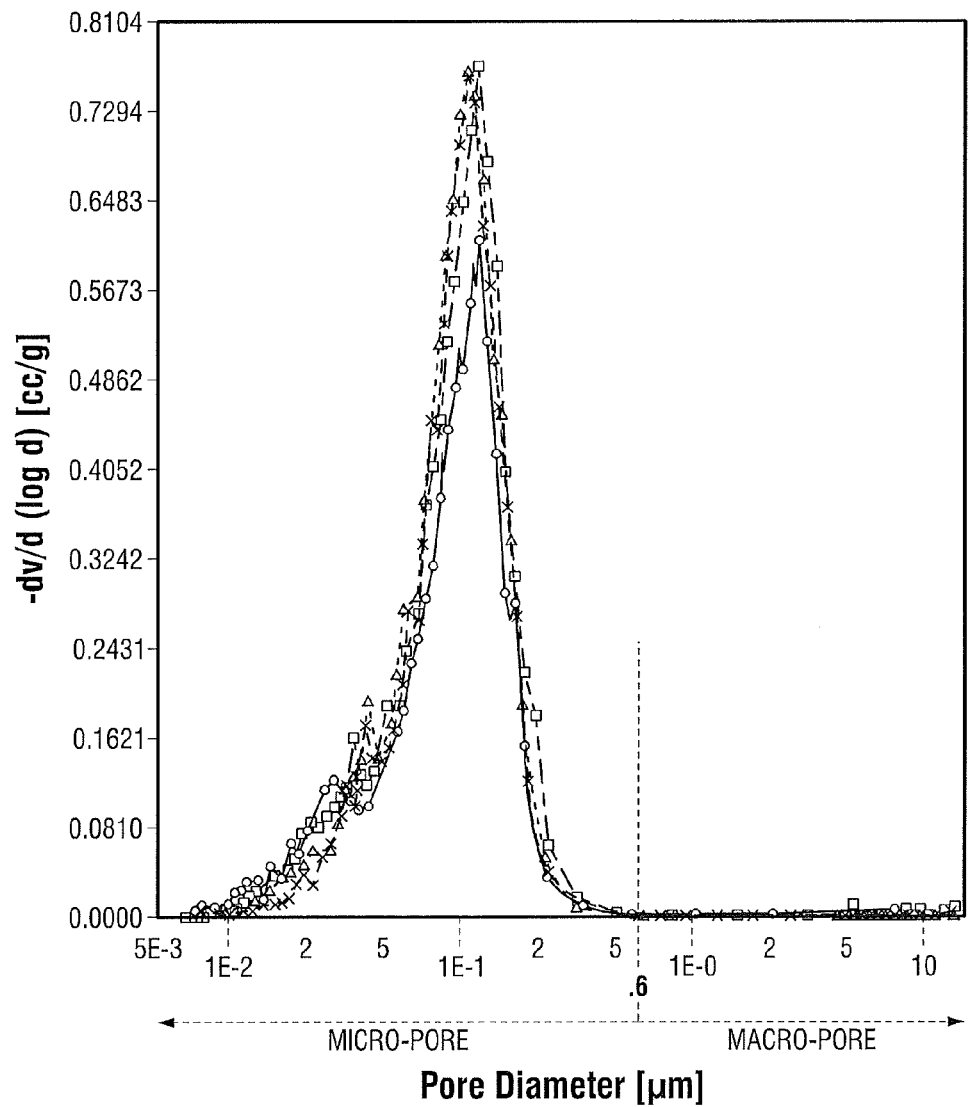
FIG. 11 illustrates another pore size distribution of original catalyst and the catalyst of this invention for Examples 11-13.
Figure 12:
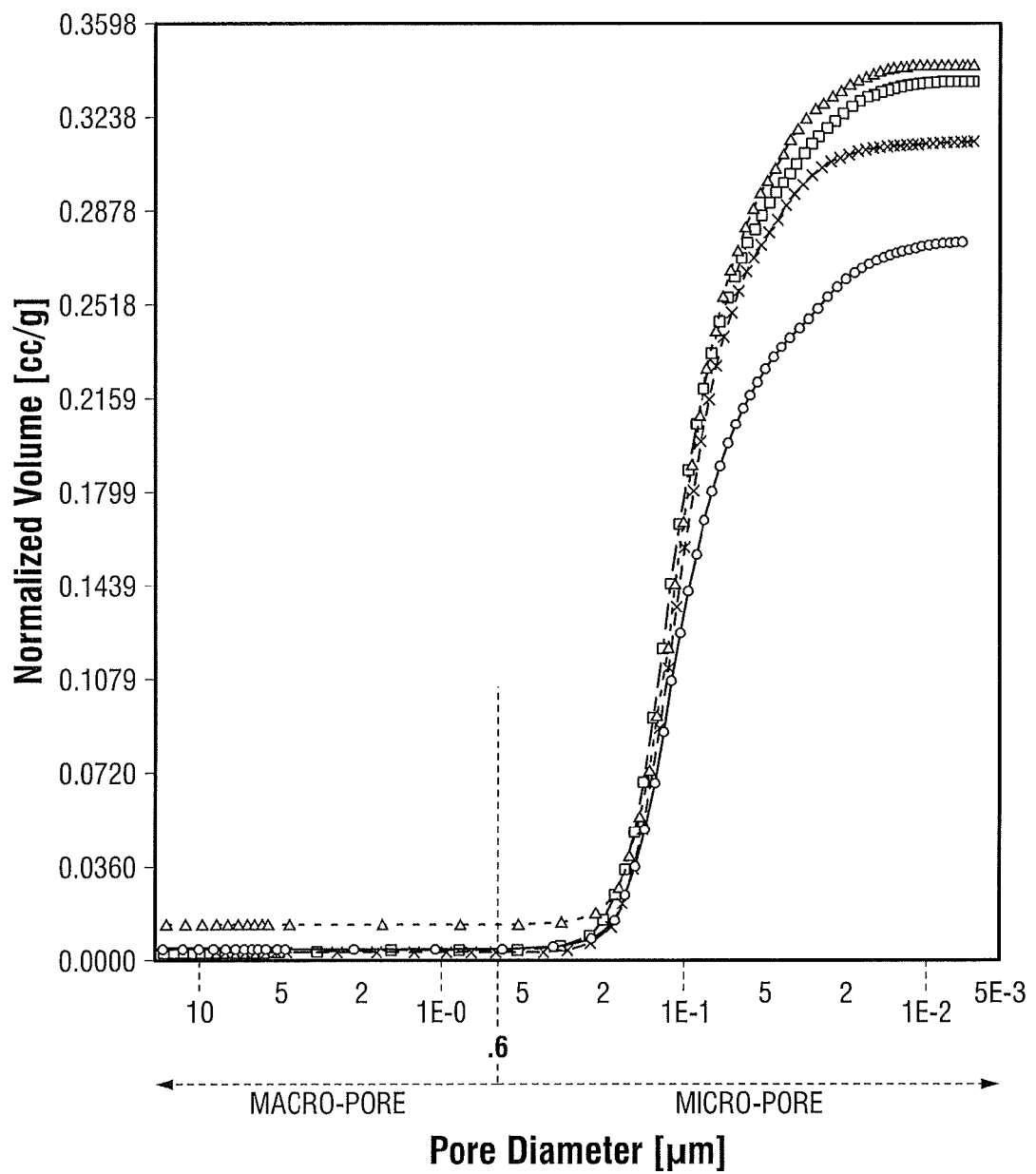
FIG. 12 illustrates the normalized pore volume vs. pore size of the original catalyst and the catalyst of present invention for Examples 11-13.

Its pore size distribution plot and normalized pore volume plot are showed in FIGS. 11 and 12, respectively.

Example 11-13

The original catalyst made in Example 10-12 was divided into three portions. About 100 g of each portion was contacted with ethylene glycol (≥99.5%, Sigma-Aldrich) in a thermal bath as described in Example 1 for different length of time period. The catalyst was treated for 2 hrs called Example 11, and the one was treated for 3 hrs called Example 12 and the one treated for 4 hrs called example 13.

Wet catalysts were put into a preheated oven at 100° C. with nitrogen purge. After dried at 100° C. for one hour, the catalysts were heated up to 190° C. and hold there for 3 h, then ramped up to 250° C. and held there for 3 h, finally cooled down to room.

Figure 13:
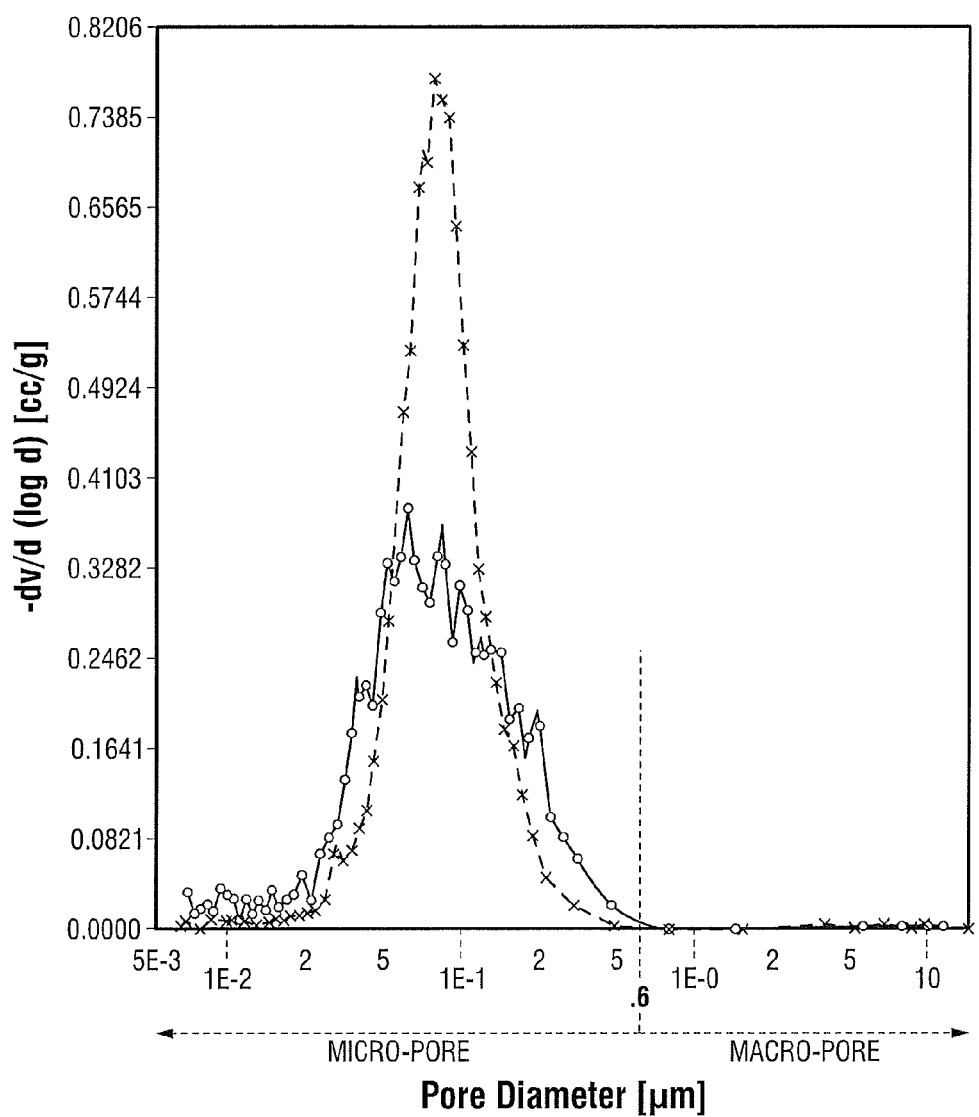
FIG. 13 illustrates another pore size distribution of original catalyst and the catalyst of this invention for Example 14.
Figure 14:
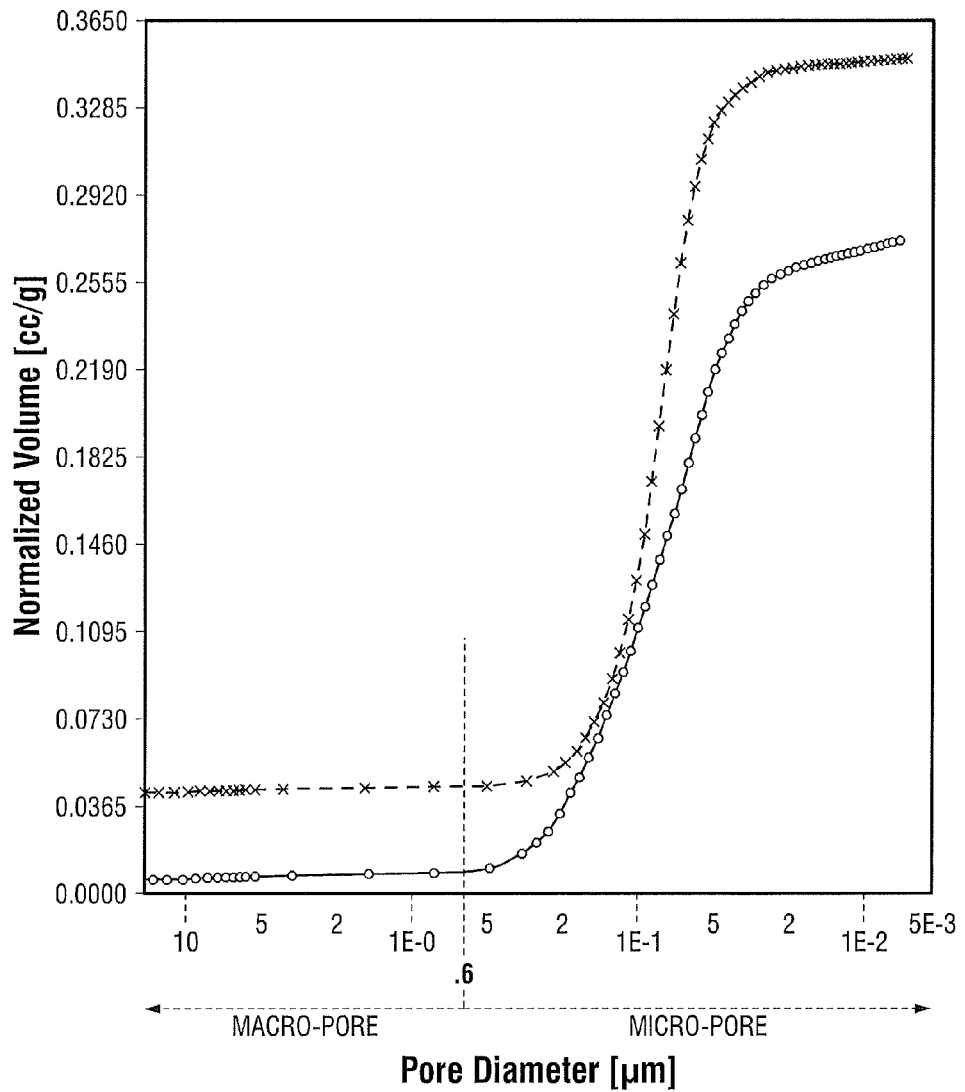
FIG. 14 illustrates the normalized pore volume vs. pore size of the original catalyst and the catalyst of present invention for Example 14.

Pore size distribution and normalized pore volume are presented in FIGS. 13 and 14, respectively.

TABLE 5

| Catalyst | BET (m2/g) | Total pore volume (cc/g) | Vp increase (%) | Vp of <0.6 microns | Vp % of <0.6 microns | Increase Vp % of <0.6 microns |
|---|---|---|---|---|---|---|
| Original for example 11-13 | 22.30 | 0.2750 | 0 | 0.2714 | 98.7 | 0 |
| Example 11 | 24.23 | 0.3131 | 13.9 | 0.3011 | 96.2 | 10.9 |
| Example 12 | 27.19 | 0.3361 | 22.2 | 0.3241 | 96.4 | 19.4 |
| Example 13 | 27.20 | 0.3426 | 24.6 | 0.3306 | 96.5 | 21.8 |

Example 14

This example demonstrates an original catalyst having different shape of tablet. This catalyst was prepared as described in Comparative Example 11-13, but the precursor was tableted into 6.35 mm cylinder with a hole through the cylinder called cored cylinder. After activation, the tablet catalyst is called the original catalyst as Comparative Example 14.

The comparative example 14 was contacted with ethylene glycol (≥99.5%, Sigma-Aldrich) in a thermal bath as described in Example 1 for 4 hr. Wet catalysts were put into a preheated oven at 100° C. with nitrogen purge. After dried at 100° C. for one hour, the catalysts were heated up to 190° C. and hold there for 3 hr, then ramped up to 250° C. and held there for 3 hr, finally cooled down to room.

Pore size distribution and normalized pore volume are presented in FIGS. 13 and 14, respectively.

TABLE 6

| Catalyst | BET (m2/g) | Total pore volume (cc/g) | Vp increase (%) | Vp of <0.6 microns | Vp % of <0.6 microns | Increase Vp % of <0.6 microns |
|---|---|---|---|---|---|---|
| Original for example 14 | 21.55 | 0.2723 | 0 | 0.2601 | 95.5 | 0 |
| Example 14 | 22.34 | 0.3477 | 27.7 | 0.3162 | 90.1 | 21.6 |

Although the present invention and its advantages have been described in detail, it should be understood that various changes, substitutions and alterations may be made herein without departing from the spirit and scope of the invention as defined by the appended claims.

What is claimed is:

1. A process for preparing a VPO catalyst comprising the steps of:
   (i) selecting an active VPO catalyst; and
   (ii) contacting the active VPO catalyst with one or more fluids comprising an organic solvent to form an active VPO catalyst having a micro-pore volume of at least 0.2 cc/g.

2. The process according to claim 1 wherein the organic solvent has a dielectric constant within a range of about 5 to about 55 when measured at a temperature of 20° C. to 25° C.

3. The process according to claim 1 wherein the organic solvent has a dielectric constant within a range of about 10 to about 50 when measured at a temperature of 20° C. to 25° C.

4. The process according to claim 1 wherein the organic solvent is selected from the group consisting of methanol, ethanol, n-propanol, n-butanol, isopropanol, isobutanol, acetonitrile, acetone, methyl ethyl ketone, DMF, dimethyly sulfoxide, tetrafuran, ethylene glycol, propylene glycol, diethylene glycol, dipropylene glycol, 1,4-butanediol, glycerin and a mixture thereof.

5. The process according to claim 1 wherein contacting is carried out at a temperature within a range from room temperature to 100° C. above the boiling point of the fluid.

6. The process according to claim 5 wherein contacting is carried out at a temperature within a range from room temperature to the boiling point of the fluid.

7. The process according to claim 1 wherein contacting is carried out a pressure ranging from atmospheric pressure to 5 bars.

8. The process according to claim 7 wherein contacting is carried out a pressure ranging from atmospheric pressure to 3 bars.

9. The process according to claim 1 further comprising drying the contacted VPO catalyst.

10. The process according to claim 1 wherein drying is carried out a temperature ranging from room temperature to 300° C.

11. The process according to claim 1 wherein drying is carried out in an atmosphere comprising air, an inert gas or a mixture thereof.

12. A process of increasing pores in a catalyst comprising the steps of:
   (i) selecting an active VPO catalyst; and
   (ii) contacting the active VPO catalyst with one or more fluids comprising an organic solvent.

* * * * *